United States Patent [19]

Tomcufcik et al.

[11] 4,259,490

[45] Mar. 31, 1981

[54] 2-(SUBSTITUTED AMINO)BENZ[CD] INDOLES

[75] Inventors: Andrew S. Tomcufcik, Old Tappan; Raymond G. Wilkinson, Montvale, both of N.J.

[73] Assignee: American Cyanamid Company, Stamford, Conn.

[21] Appl. No.: 161,709

[22] Filed: Jun. 23, 1980

Related U.S. Application Data

[63] Continuation-in-part of Ser. No. 91,086, Nov. 23, 1979, abandoned.

[51] Int. Cl.³ .................. A61K 31/495; C07D 403/04
[52] U.S. Cl. .................................. 544/369; 424/250; 544/372
[58] Field of Search .......................... 544/369; 544/372

[56] References Cited

U.S. PATENT DOCUMENTS

| Re. 29,834 | 11/1978 | Brack et al. | 544/372 |
| 3,705,161 | 12/1972 | Razdan et al. | 544/372 |

FOREIGN PATENT DOCUMENTS 1432660  4/1976  United Kingdom ................ 544/369

Primary Examiner—Donald G. Daus
Assistant Examiner—James H. Turnipseed
Attorney, Agent, or Firm—Edward A. Conroy, Jr.

[57] ABSTRACT

Novel 2-(substituted amino)benz[cd]indoles useful as inhibitors of platelet aggregation and the process for their preparation.

6 Claims, No Drawings

2-(SUBSTITUTEDAMINO)BENZ[CD]INDOLES

CROSS REFERENCE TO RELATED APPLICATION

This application is a continuation-in-part of our co-pending application Ser. No. 97,086, filed Nov. 23, 1979, now abandoned.

DESCRIPTION OF THE INVENTION

This invention is concerned with new 2-(substituted amino)benz[cd]indoles of the formula:

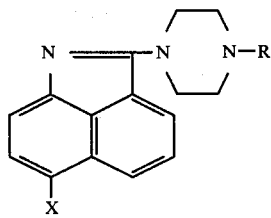

R is selected from the group consisting of methyl, benzyl, benzoyl, 3-dimethylaminopropyl and 2-thiazolyl; X is selected from the group consisting of hydrogen, chloro and bromo and the pharmaceutically acceptable acid-addition salts thereof.

The compounds of the present invention may be prepared according to the following flowchart:

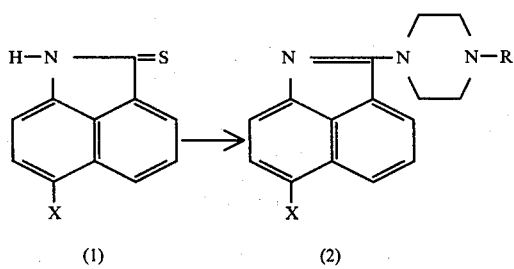

A substituted benz[cd]indol-2-thione (1) is refluxed in a solvent such as benzene, toluene, dioxane or 1,2-dimethoxyethane and treated successively with a reagent such as N-(2-thiazolyl)piperazine, N-methylpiperazine, N-benzylpiperazine or N-benzoylpiperazine, followed by mercuric acetate. The mixture is refluxed for 30 minutes to three hours, filtered and the filtrate evaporated. The residue is treated with an aqueous base, extracted with chloroform and the extracts treated with ethanolic hydrogen chloride to produce the hydrochloride salt of the desired compounds (2) where X and R are as hereinabove described.

The aggregation of blood platelets is an important mechanism in thrombosis and as the degree of aggregation increases the tendency of thrombus formation also increases. The compounds of the present invention inhibit the aggregation of blood platelets and thus are useful as antithrombotic agents in the treatment of well known thrombotic conditions resulting from platelet aggregation. Such conditions include, for example, arterial thrombosis, pulmonary embolism, cerebrovascular disease, rheumatic heart disease, myocardial infarction, thromophlebitis or thromboembolic conditions which may develop spontaneously following surgery, trauma or disease processes such as coronary occlusion and congestive heart failure. They may also be useful in reducing transient ischematic attacks of the brain and possibly the heart, as well as extrinsically in preventing the clotting of shed and/or stored blood.

The compounds were tested essentially according to the method of G.V.R. Born, Nature, No. 4832, 927–929 (1962) and J. R. O'Brien, J. Clin, Path., 15, 446–452 (1962). Various concentrations of the test compounds were added in vitro to human platelet rich plasma. Collagen (final concentration 500 mcg./ml.), adenosine diphosphate (final concentration 1 to $4 \times 10^{-6}$ M) or sodium arachidonate (final concentration 0.5 mM to 1.0 mM) was added to induce platelet aggregation. Inhibition of platelet aggregation was determined by measuring the change in the optical density of the platelet rich plasma as compared to control plasma. Test compounds showing inhibition at final concentrations of 25 mcg./ml. or less are considered active.

Table I records the results of this test with representative compounds of this invention.

TABLE I

| Compound | Result |
| --- | --- |
| 2-(4-Methyl-1-piperazinyl)benz[cd]indole dihydrochloride | Active |
| 2-(4-Benzyl-1-piperazinyl)benz[cd]indole dihydrochloride | Active |
| 2-[4-(2-Thiazolyl)-1-piperazinyl]benz[cd]indole dihydrochloride | Active |
| 1-Benzoyl-4-(6-bromobenz[cd]indol-2-yl)-piperazine | Active |
| 2-[4-(3-Dimethylaminopropyl)-1-piperazinyl]benz[cd]indole trihydrochloride | Active |

In a second test, in vivo activity of the compounds as platelet aggregation inhibitors were established. In this test the compounds were administered orally to male rats at doses ranging from 0.1 mg./kg. to 100 mg./kg. of body weight. After an interval of 1 to 2 hours or more the rats were bled and platelet rich plasma obtained. Collagen (final concentration 500 mcg./ml.) or adenosine diphosphate (final concentration 1 to $4 \times 10^{-6}$ M) was added to induce platelet aggregation and comparisons were made between control and treated samples. A compound is considered active if it inhibits aggregation by 30% or more at a dose of 1 to 10 mg./kg. of body weight.

Table II records the results of this test with representative compounds of this invention.

TABLE II

| Compound | Result |
| --- | --- |
| 2-(4-Methyl-1-piperazinyl)benz[cd]indole dihydrochloride | Active |
| 2-(4-Benzyl-1-piperazinyl)benz[cd]indole dihydrochloride | Active |
| 2-[4-(2-Thiazolyl)-1-piperazinyl]benz[cd]indole dihydrochloride | Active |
| 1-Benzoyl-4-(6-bromobenz[cd]indol-2-yl)-piperazine | Active |
| 2-[4-(3-Dimethylaminopropyl)-1-piperazinyl]benz[cd]indole trihydrochloride | Active |

EXAMPLE 1

2-(4-Methyl-1-piperazinyl)benz[cd]indole dihydrochloride

The subject compound is prepared essentially by the procedure set forth on page 2 using an equivalent of N-methylpiperazine. Recrystallization from aqueous methanol gives the pure dihydrochloride, melting at 291°–293° C. with decomposition.

EXAMPLE 2

2-(4-Benzyl-1-piperazinyl)benz[cd]indole dihydrochloride

The subject compound is prepared essentially by the procedure of Example 1, an equivalent of N-benzyl-piperazine replacing the N-methylpiperazine. The crude dihydrochloride is purified by recrystallization from aqueous ethanol and melted at 260°–263° C. with decomposition.

EXAMPLE 3

2-[4-(2-Thiazolyl)-1-piperazinyl]benz]cd]indole dihydrochloride

The title compound is prepared essentially by the procedure of Example 1, an equivalent of N-(2-thiazolyl)piperazine replacing the N-methylpiperazine. The dihydrochloride is isolated by solution in ethanol and reprecipitated with diethylether. It melts at 246°–248° C. with decomposition.

EXAMPLE 4

1-Benzoyl-4-(6-bromobenz[cd]indol-2-yl)piperazine

Ethyl 4-(6-bromobenz[cd]indol-2-yl)piperazine-1-carboxylate is prepared essentially by the procedure of Example 1, an equivalent of ethyl piperazine-1-carboxylate replacing the N-methylpiperazine. It is purified as the free base by recrystallization from benzene-hexane, and melts at 170°–174° C.

A 6 g. portion of the above ester is added to 70 ml. of 48% hydrobromic acid and the mixture stirred and heated under reflux until a clear solution results (about two hours). The solution is cooled at 5° C., causing the formation of a bright yellow precipitate of the dihydrobromide of 1-(6-bromobenz[cd]indol-2-yl)piperazine. This is dissolved in water, the solution made basic with 5 N sodium hydroxide, and the mixture then extracted with chloroform. The chloroform solution is dried over sodium sulfate. Addition of excess ethanolic hydrogen chloride gives a precipitate of the dihydrochloride salt, melting at 305°–310° C. with decomposition.

A mixture consisting of 7.1 g. of 1-(6-bromobenz-[cd]indol-2-yl)piperazine, 75 ml. of water, and 75 ml. of chloroform is stirred vigorously as 10 ml. of 5 N soidum hydroxide is added, followed by 5 g. of benzoyl chloride, in six portions over a period of 10 minutes. The reaction mixture is stirred an additional 30 minutes after the completion of the benzoyl chloride addition. The chloroform layer is separated and dried over sodium sulrate. After separation from impurities by chromatography on an alumina column, the title compound is recrystallized from benzene-chloroform to yield orange flakes, melting at 237.5°–239° C.

EXAMPLE 5

2-[4-(3-Dimethylaminopropyl)-1-piperazinyl]benz[cd]indole trihydrochloride

The free base of the title compound is prepared essentially by the procedure of Example 1, an equivalent of 1-(3-dimethylaminopropyl)piperazine replacing the N-methylpiperazine. The trihydrochloride salt is prepared by treatment with ethanolic hydrogen chloride. Recrystallization from aqueous methanol gives yellow crystals, melting at 300°–302° C. with decomposition.

We claim:

1. A compound selected from the group consisting of those of the formula:

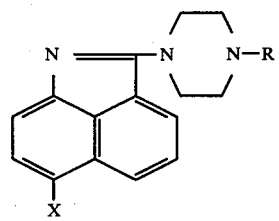

wherein R is selected from the group consisting of methyl, benzyl, benzoyl, 3-dimethylaminopropyl and 2-thiazolyl and X is selected from the group consisting of hydrogen, chloro and bromo; and the pharmaceutically acceptable acid-addition salts thereof 2. The compound according to claim 1; 2-(4-methyl-1-piperazinyl)benz[cd]indole dihydrochloride.

3. The compound according to claim 1; 2-(4-benzyl-1-piperazinyl)benz[cd]indole dihydrochloride.

4. The compound according to claim 1; 2-[4-(2-thiazolyl)-1-piperazinyl]-benz[cd]indole dihydrochloride.

5. The compound according to claim 1; 1-benzoyl-4-(6-bromobenz[cd]indol-2-yl)piperazine.

6. The compound according to claim 1; 2-[4-(3-dimethylaminopropyl)-1-piperazinyl]benz[cd]indole trihydrochloride.

* * * * *